US011193105B2

(12) United States Patent
Macquart et al.

(10) Patent No.: US 11,193,105 B2
(45) Date of Patent: Dec. 7, 2021

(54) MICROALGAL BIOMASS PROTEIN ENRICHMENT METHOD

(71) Applicant: Corbion Biotech, Inc., South San Francisco, CA (US)

(72) Inventors: Gabriel Macquart, Mont Bernanchon (FR); Sylvain Delaroche, Longuenesse (FR); Marie Le Ruyet, Lille (FR); Laurent Segueilha, Marquette lez Lille (FR)

(73) Assignee: Corbion Biotech, Inc., South San Francisco, CA (US)

( * ) Notice: Subject to any disclaimer, the term of this patent is extended or adjusted under 35 U.S.C. 154(b) by 0 days.

(21) Appl. No.: 16/254,463

(22) Filed: Jan. 22, 2019

(65) Prior Publication Data

US 2019/0218503 A1    Jul. 18, 2019

Related U.S. Application Data

(63) Continuation of application No. 14/779,365, filed as application No. PCT/EP2014/056125 on Mar. 27, 2014, now abandoned.

(30) Foreign Application Priority Data

Mar. 29, 2013  (FR) ...................................... 1352857
Aug. 19, 2013  (FR) ...................................... 1358052

(51) Int. Cl.
    *C12N 1/12*     (2006.01)
    *C12P 21/00*    (2006.01)

(52) U.S. Cl.
    CPC ............... *C12N 1/12* (2013.01); *C12P 21/00* (2013.01)

(58) Field of Classification Search
    None
    See application file for complete search history.

(56) References Cited

U.S. PATENT DOCUMENTS

| | | | |
|---|---|---|---|
| 2,949,700 | A | 8/1960 | Kathrein |
| 3,108,402 | A | 10/1963 | Kathrein |
| 3,142,135 | A | 7/1964 | Kathrein |
| 3,962,466 | A | 6/1976 | Nakabayashi |
| 4,564,526 | A | 1/1986 | Takashima |
| 5,547,699 | A | 8/1996 | Iizuka et al. |
| 5,792,631 | A | 8/1998 | Running |
| 5,912,113 | A | 6/1999 | Nakamura et al. |
| 2007/0099280 | A1 | 5/2007 | Barclay |
| 2007/0167396 | A1 | 7/2007 | Dillon et al. |
| 2010/0297292 | A1 | 11/2010 | Brooks et al. |
| 2010/0297295 | A1 | 11/2010 | Brooks et al. |
| 2010/0297296 | A1 | 11/2010 | Brooks et al. |
| 2010/0297323 | A1 | 11/2010 | Brooks et al. |
| 2010/0297325 | A1 | 11/2010 | Brooks et al. |
| 2010/0297331 | A1 | 11/2010 | Brooks et al. |
| 2010/0303957 | A1 | 12/2010 | Brooks et al. |
| 2010/0303961 | A1 | 12/2010 | Brooks et al. |
| 2010/0303989 | A1* | 12/2010 | Brooks .................. A21D 2/165 426/541 |
| 2010/0303990 | A1 | 12/2010 | Brooks et al. |
| 2012/0128851 | A1 | 5/2012 | Brooks et al. |
| 2013/0122180 | A1 | 5/2013 | Brooks et al. |
| 2016/0046900 | A1 | 2/2016 | Macquart et al. |
| 2016/0143336 | A1 | 5/2016 | Druon et al. |
| 2016/0161460 | A1 | 6/2016 | Druon et al. |
| 2016/0192691 | A1 | 7/2016 | Druon et al. |
| 2016/0208212 | A1 | 7/2016 | Delaroche et al. |
| 2016/0324167 | A1 | 11/2016 | Brooks et al. |
| 2016/0326483 | A1 | 11/2016 | Segueilha et al. |
| 2016/0340640 | A1 | 11/2016 | Macquart et al. |
| 2016/0376544 | A1 | 12/2016 | Cossart et al. |
| 2018/0139994 | A1 | 5/2018 | Brooks et al. |
| 2018/0230421 | A1 | 8/2018 | Macquart et al. |
| 2018/0312798 | A1 | 11/2018 | Segueilha et al. |

FOREIGN PATENT DOCUMENTS

| | | |
|---|---|---|
| CN | 101230364 A | 7/2008 |
| CN | 102618431 | 8/2012 |
| EP | 1 142 985 A1 | 10/2001 |
| EP | 1 359 224 A1 | 11/2003 |
| EP | 1 724 357 | 11/2006 |
| EP | 2 248 906 | 11/2010 |
| FR | 1356113 | 3/1964 |
| FR | 2 924 126 A1 | 5/2009 |
| JP | 360075244 | 10/1983 |
| JP | 409252707 A | 9/1997 |
| JP | 2000-175680 A | 6/2000 |
| JP | 2002-223787 A | 8/2002 |
| WO | WO 2010/045368 | 4/2010 |

(Continued)

OTHER PUBLICATIONS

Ji et al. Limnology and Oceanography, 2008, vol. 53, No. 5, pp. 1790-1804.*
Sansawa et al. Journal of Bioscience and Bioengineering. 2004, vol. 98, No. 6, pp. 437-444.*
Non-Final Rejection, dated Jan. 11, 2017, in U.S. Appl. No. 14/779,365.
Final Rejection, dated Sep. 14, 2017, in U.S. Appl. No. 14/779,365.
Non-Final Rejection, dated Apr. 27, 2018, in U.S. Appl. No. 14/779,365.
Final Rejection, dated Oct. 31, 2018, in U.S. Appl. No. 14/779,365.
Non-Final Rejection, dated Jul. 28, 2017, in U.S. Appl. No. 14/911,078.
Final Rejection, dated Jan. 26, 2018, in U.S. Appl. No. 14/911,078.
Restriction Requirement, dated Oct. 30, 2017, in U.S. Appl. No. 14/911,743.
Non-Final Rejection, dated Jun. 6, 2018, in U.S. Appl. No. 14/911,743.
Non-Final Rejection, dated Apr. 13, 2017, in U.S. Appl. No. 14/913,383.

(Continued)

*Primary Examiner* — Vera Afremova
(74) *Attorney, Agent, or Firm* — Leydig, Voit & Mayer

(57) ABSTRACT

The invention relates to a method for protein enrichment of a microalga grown under heterotrophic conditions, said microalga being of the *Chlorella* genus, characterized in that the heterotrophic culture comprises a step aimed at limiting the growth of said microalga by means of a deficiency of the fermentation medium in terms of a non-nitrogenous nutritional source.

9 Claims, No Drawings

(56) References Cited

FOREIGN PATENT DOCUMENTS

| WO | WO 2010/120923 | | 10/2010 |
|---|---|---|---|
| WO | WO 2011/130578 | A2 | 10/2011 |
| WO | WO 2012/063137 | | 5/2012 |
| WO | WO 2014/074769 | A2 | 5/2014 |
| WO | WO 2014/117163 | A1 | 7/2014 |
| WO | WO 2014/154787 | | 10/2014 |
| WO | WO 2014/207376 | | 12/2014 |
| WO | WO 2014/207377 | | 12/2014 |
| WO | WO 2015/011428 | | 1/2015 |
| WO | WO 2015/022469 | | 2/2015 |
| WO | WO 2015/025111 | | 2/2015 |
| WO | WO 2015/079182 | | 6/2015 |
| WO | WO 2015/107312 | | 7/2015 |
| WO | WO 2017/137668 | | 8/2017 |

OTHER PUBLICATIONS

Final Rejection, dated Dec. 26, 2017, in U.S. Appl. No. 14/913,383.
Non-Final Rejection, dated Jan. 13, 2017, in U.S. Appl. No. 15/039,428.
Final Rejection, dated Jul. 11, 2017, in U.S. Appl. No. 15/039,428.
Non-Final Rejection, dated Jan. 5, 2018, in U.S. Appl. No. 15/039,428.
Restriction Requirement, dated Jan. 19, 2017, in U.S. Appl. No. 15/112,436.
Non-Final Rejection, dated Apr. 6, 2017, in U.S. Appl. No. 15/112,436.
Final Rejection, dated Oct. 16, 2017, in U.S. Appl. No. 15/112,436.
International Search Report, dated Sep. 30, 2014, from International Patent Application No. PCT/EP2014/056125, pp. 1-8.
Written Opinion of the Searching Authority, dated Sep. 30, 2014, from International Patent Application No. PCT/EP2014/056125, pp. 1-8.
International Search Report, dated Nov. 24, 2014, from International Patent Application No. PCT/FR2014/051943.
Written Opinion of the Searching Authority, dated Nov. 24, 2014, from International Patent Application No. PCT/FR2014/051943.
International Search Report, dated Feb. 11, 2015, from International Patent Application No. PCT/FR2014/052081.
Written Opinion of the Searching Authority, dated Feb. 11, 2015, from International Patent Application No. PCT/FR2014/052081.
International Search Report, dated Nov. 20, 2014, from International Patent Application No. PCT/FR2014/052113.
Written Opinion of the Searching Authority, dated Nov. 20, 2014, from International Patent Application No. PCT/FR2014/052113.
International Search Report, dated Mar. 10, 2015, from International Patent Application No. PCT/FR2014/053075.
Written Opinion of the Searching Authority, dated Mar. 10, 2015, from International Patent Application No. PCT/FR2014/053075.
International Search Report, dated Jun. 1, 2015, for International Patent Application No. PCT/FR2015/050123, pp. 1-14.
Written Opinion, dated Jun. 1, 2015, for International Patent Application No. PCT/FR2015/050123, pp. 1-14.
International Search Report, dated Sep. 5, 2016, from International Patent Application No. PCT/FR2016/050269, filed Feb. 8, 2016, and English Translation.
Written Opinion of the Searching Authority, dated Sep. 5, 2016, from International Patent Application No. PCT/FR2016/050269, filed Feb. 8, 2016. No Translation.
Chinese Patent Application No. 201480039481.5, Notification of First Office Action, dated Jul. 5, 2017.
Chinese Patent Application No. 201480039481.5, Notification of Second Office Action, dated May 9, 2018.
Japanese Patent Application No. JP 2016-533941, English Translation of the Notice of Reasons for Rejection, dated May 21, 2018, with English Translation.
European Patent Application No. EP3036316, First Examination Report, dated Oct. 10, 2017. (in French).
Japanese Patent Application No. JP 2016-535517, English Translation of the Notice of Reasons for Rejection, dated May 21, 2018.

Albuquerque, M.G.E., et al., "Strategies for the development of a side stream process for polyhydroxyalkanoate (PHA) production form sugar case molasses." Journal of Biotechnology (2007), 130: 411-421, Specif, pp. 412, 415, 417.
Anderson, *Algal Culturing Techniques*, Elsevier, (2005), Part 1.
Anderson, *Algal Culturing Techniques*, Elsevier, (2005), Part 2, with Examiner's. Notes, p. 433.
Becker, E.W., "Micro-algae as a source of protein," Biotechnology Advances,vol. 25; No. 2, pp. 207-201, (Jan. 26, 2007).
Belasco, Warren, "Algae Burgers for a Hungry World? The Rise and Fall of Chlorella Cuisine," Technology and Culture, 38(3):608-634, (1997).
Brown, M.R., et al. "Biochemical composition of microalgae from the green algal classes Chlorophyceae and Prasinophyæae. 1. Amino acids, sugars and pigments" *Journal of Experimental Marine Biology and Ecology*, (Oct. 12, 1992), 161(1), 91-113.
Chacón-Lee, T.L. and G.E. González-Mariño, "Microalgae for "Healthy" Foods—Possibilities and Challenges", Comprehensive Reviews in Food Science and Food Safety, vol. 9; (Oct. 31, 2010), pp. 655-675.
Chen, Y.H., et al., "Fed-batch fermentation and supercritical fluid extraction of heterotrophic microalgal *Chlorella protothecoides*lipids", Bioresourse Technology, Jun. 1, 2012), vol. 114, pp. 512-517.
Doucha , J. et al., "Production of High-density Chlorella culture grown in fermenters", Journal of Applied Phycology, Jan. 12, 2011, vol. 24, No. 1, pp. 35-43.
Guccione, Alessia et al., "Chlorella for protein and biofuels: from strain selection to otdoor cultivation in a Green Wall Panel photobioreactor", Biotechnology for Biofuels, Biomed Central, Ltd, GB, (Jun. 7, 2014), vol. 8, No. 1, p. 84.
Harms, P., et al., "Bioprocessing monitoring", *Current Opinion in Biotechnology*, Apr. 1, 2002, vol. 13, No. 2, pp. 124-127.
Ji, Y. et al. "Differential effects of phosphorus limitation on cellular metals in Chlorella and Microcystis" Limnology and Oceanography, (Sep. 1, 2008), vol. 53, No. 5., pp. 1790-1804.
Kliphuis, A.M.J. et al., "Light respiration in Chlorella sorokiniana". Journal of Applied Phycology, (2011), 23:935-947 (specif, pp. 935, 937, 938, 945).
Krüger, "Kurze Charakteristik einiger niedrerer Organismen im Saftfluss der Laubbäaume," Hedwigia, 33: 241-266, (1894), Machine Translation.
Li, Xiufeng, et al., "Large-scale biodiesel production from microalga *Chlorella protothecoides* through heterotrophic cultivation in bioreactors," Biotechnology and Bioengineering, 98(04):764-771, (Nov. 1, 2007).
Mattes, R.D., "Is there a fatty acid taste?" Annual Review of Nutrition, (2009), 29:305-327 (cited pre-pub manuscript, pp. 1-24, specif, p. 7.).
Miao et al., "Biodiesel Production From Heterotrophic Microalgal Oil," Biosource Technology, 97(06):841-846, (2006).
Miao et al., "High Yield Bio-Oil Production from Fast Pyrolysis by Metabolic Controlling of Chlorella Protothecoides," J. Biotech., 110:85-93, (2004).
Perez-Garcia, O. et al., "Heterotrophic cultures of microalgae: Metabolism and potential products", Water Research, Jan. 1, 2011, vol. 45, No. 1, pp. 11-36.
Pleissner, D. et a l. Effects of Phosphorous, Nitrogen, and Carbon Limitation on Biomass Composition in Batch and Continuous Flow Cultures of the Heterotrophic Dinoflagellate Crypthecodinium cohnil' Biotechnology and Bioengineering, Aug. 2012,pp. 2005-2016, vol. 109, No. 8.
Qu, C.-B. et al. "Phosphate assimilation by Chlorella and adjustment of phosphate concentration in basal medium for its cultivation" Biotechnology Letters, Oct. 20, 2008, pp. 1735-1740, vol. 30, No. 10.
Rhee, G-Yull, "Effects of N:P Atomic Ratios and Nitrate Limitation on Algal Growth, Cell Composition, and Nitrate Uptake", Limnology and Oceanography, vol. 23, No. 1 (Jan. 1978), pp. 10-25.
Samarasinghe, Nalin, et al., "Algal Cell Rupture Using High Pressure Homogenization as a Prelude to Oil Extraction." Renewable Energy, vol. 48, (Apr. 20, 2012) pp. 300-308, 2012.

(56) References Cited

OTHER PUBLICATIONS

Sansawa, H. et al., "Production of Intracellular Phytochemicals in Chlorella under Heterotrophic Conditions," Journal of Bioscience and Bioengineering, 98(6):437-444, (Jan. 1, 2004).

Shi et al., "Production and rapid extraction of lutein and the other lipid-soluble pigments from Chlorella protothecoides grown under heterotrophic and mixotrophic conditions," Nahrung, 43:109-113, (1999).

Shi, et al., "Production of biomass and lutein by Chlorella protothecoides at various glucose concentrations in heterotrophic cultures", Process Biochemistry, 34:341-347, (1999).

Shi, X. M. et al., "High-Yield Production of Lutein by the Green Microalga *Chlorella protothecoides* in Heterotrophic Fed-Batch Culture," Biotechnol. Prog., 18(4):723-727 (2002).

Shihira-Ishikawa, I., et al., "Nutritional Control of Cell Pigmentation In Chlorella Protothecoides With Special Reference to The Degeneration of Chloroplast Induced by Glucose," Plant and Cell Physiology, 5(2):227-240 (Feb. 1, 1964), [online abstract], Retrieved on Jun. 3, 2010 from http://pcp.oxfordjounals.org/cgi/content/abstract/5/2/227.

Suh, I.S. et al., "Photobioreactor Engineering: Design and Performance", Biotechnology and Bioprocess Engineering, (Jan. 1, 2003), vol. 8, No. 6, pp. 313-321.

Syrett, P.J., "The Assimilation of Ammonia by Nitrogen-Starved Cells of Chlorella Vulgaris. Part II. The Assimilation of Ammonia to Other Compounds." Annals of Botany, vol. 17, pp. 21-36, 1953.

Syrett, P.J., "The Assimilation of Ammonia by Nitrogen-Straved Celled of Chlorella vulgaris. Part I: The Correlation of Assimilation with Respiration", Annals of Botany, Academic Press, London, GB,(Jan. 1, 1953), vol. 17, No. 1, pp. 1-19.

Watson, Elaine, et al., "Solazyme Breaking News on Food & Beverage Development—North America Special Edition: Protein-Rich Foods . . . The Next Generation Could Algae be the Next Big Thing in Protein Market? Part one: Solazyme Roquette Nutritionals." URL:http://www.foodnavigator-usa.com/contenUview/prinU733996, Jan. 23, 2013.

Wu et al., "A Comparative Study of Gases Generated from Simulant Thermal Degradation of Autotrophic and Heterotrophic Chlorella," Progress in Natural Science, 2(4):311-318, (1992).

Wu et al., "Comparative study on Liposoluble Compounds in Autotrophic and Heterotrophic Chlorella Protothecoides," Acta Botanica Sinica, 35(11):849-858, (1992).

Wu et al., "New Discoveries in Study on Hydrocarbons From Thermal Degradation of Heterotrophically Yellowing Algae," Science In China, 37(3):326-35, (Mar. 1, 1994).

Xiong et al., "High-density fermentation of microalga *Chlorella protothecoides* in bioreactor for microbio-diesel production," Appl. Microbiol. Biotechnol., 78:29-36, (2008).

Xu, H., et al., "High Quality Biodiesel Production from a Microalgal Chlorella Protothecoides by Heterotrophic Growth in Fermenters." Journal of Biotechnology, vol. 126, pp. 499-507, (2006).

Zeng, A.P. et al., "Use of respratory quotient as a control parameter for optimum oxygen supply and scale-up of 2,3-butanediol production undermicroaerobic conditions." Biotechnology and Bioengineering, (1994), 44:1107-1114.

Li, Xiufeng, et al., "Large-Scale Biodiesel Production From Microalga Chlorella protothecoides Through Heterotrophic Cultivation in Bioreactors", Biotechnology and Bioengineering, (Dec. 31, 2007), vol. 98, No. 4, pp. 764-771.

Qianran, Ma et al., "The Fermenter High Density Heterotrophic Culture of Chlorella", Guangdong Chemical Industry, (Feb. 28, 2013), Issue 40, vol. 4 (English Abstract Only).

Chen et al., (1991) "Effect of C/N ratio and aeration on the fatty acid composition of heterotrophic *Chlorella sorokiniana*," *Journal of Applied Phycology*, 3:203-209.

Memorandum Order, *Roquette Frères, S.A. v. Solazyme, Inc.*, C.A. No. 14-1442-SLR, District Court for the District of Delaware, Jan. 12, 2016.

Plaintiff and Counter-Defendant Roquette Frères, S.A.'s Reply Brief in Support of Its Motion for Stay Pending Appeal, *Roquette Frères, S.A. v. Solazyme, Inc.*, C.A. No. 14-1442-SLR, District Court for the District of Delaware, Jan. 8, 2016.

Defendant and Counterclaimant Solazyme, Inc.'s Brief in Opposition To Plaintiff and Counter-Defendant Roquette Freres, S.A.'s Motion to Stay Pending Appeal, *Roquette Frères, S.A. v. Solazyme, Inc.*, C.A. No. 14-1442-SLR, District Court for the District of Delaware, Jan. 6, 2016.

Declaration of Jonathan Wolfson in Support of Defendant and Counterclaimant Solazyme, Inc.'s Opposition to Plaintiff and Counterclaimant Roquette Freres, S.A.'s Motion to Stay Pending Appeal, *Roquette Frères, S.A. v. Solazyme, Inc.*, C.A. No. 14-1442-SLR, District Court for the District of Delaware, Jan. 6, 2016, Redacted Public Version.

Declaration of Jeffrey M. Goehring in Support of Plaintiff and Counter-Defendant Roquette Frères, S.A.'s Brief Motion for Stay Pending Appeal, *Roquette Frères, S.A. v. Solazyme, Inc.*, C.A. No. 14-1442-SLR, District Court for the District of Delaware, Dec. 28, 2015, Redacted Version • Exhibit 1, BASF and Solazyme Launch the First Commercial Microalgae-Derived Betaine Surfactant, Solazyme, Inc., Jul. 28, 2015 • Exhibit 2, Solazyme Bunge Renewable Oils Completes Key Redundant Power and Steam Supplies, Solazyme Bunge Renewable Oils, Jun. 30, 2015 • Exhibit 3, Solazyme Receives FDA GRAS No Questions Letter for High Oleic Algae Oil, Solazyme, Inc., Feb. 24, 2015 • Exhibit 4, Solazyme's (SZYM) CEO Jonathan Wolfson on Q1 2015 Results—Earnings Call Transcript, Solazyme, Inc., May 6, 2015 • Exhibit 5, Solazyme's (SZYM) CEO Jonathan Wolfson on Q2 2015 Results—Earnings Call Transcript, Solazyme, Inc., Jul. 30, 2015 • Exhibit 6, Solazyme's (SZYM) CEO Jonathan Wolfson on Q4 2014 Results—Earnings Call Transcript, Solazyme, Feb. 26, 2015 • Exhibit 7, Redacted In Its Entirety.

Motion To Stay Pending Appeal and Order Granting Motion to Stay Pending Appeal, *Roquette Frères, S.A. v. Solazyme, Inc.*, C.A. No. 14-1442-SLR, District Court for the District of Delaware, Dec. 28, 2015.

Memorandum of Law in Support of Motion By Roquette Frères, S.A. For a Stay Pending Appeal, *Roquette Frères, S.A. v. Solazyme, Inc.*, C.A. No. 14-1442-SLR, District Court for the District of Delaware, Dec. 28, 2015.

Email dated Nov. 3, 2015, from Gerald Suh of Solazyme, Inc., to Jeffrey M. Goehring of Young & Thompson International Patent & Trademark Law (counsel for Roquette Frères, S.A.).

Letter dated Oct. 6, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the following enclosures: • Exhibits 1, 9-12, and 14-15 To the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc.*, C.A. No. 14-01442, District Court for the District of Delaware, D.I. 141, Jun. 22, 2015, Redacted Version • Exhibits 2-8 to the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 112-1, Jun. 22, 2015 • Exhibit 13 To the Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 112-2, Jun. 22, 2015 • Declaration of Jeffrey M. Goehring in Support of Roquette Frères, S.A.'s Brief in Support of Its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 112, Jun. 22, 2015 • Roquette Frères, S.A.'s Opening Brief in Support of Its Motion for Summary Judgment of Solazyme, Inc.'s Claim for Misappropriation of Trade Secrets, *Roquette Frères, S.A. v. Solazyme, Inc., C.A.* No. 14-01442, District Court for the District of Delaware, D.I. 140, Jun. 22, 2015, Redacted Version.

(56) References Cited

OTHER PUBLICATIONS

Letter dated Nov. 2, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC), which included the same enclosures included with the letter dated Oct. 6, 2015 of Cite No. CB.

Email dated Nov. 4, 2015, from Jeffrey M. Goehring of Young & Thompson International Patent & Trademark Law (counsel for Roquette Frères, S.A.) to Gerald Suh of Solazyme, Inc., and R. James Balls and William E. McShane of Novak Druce Connolly Bove + Quigg LLP (counsel for Solazyme Roquette Nutritionals, LLC).

Opinion dated Dec. 21, 2015 in *Roquette Frères, S.A.*, v. *Solazyme, Inc.*, Case No. 1:14-cv-01442 (D. Del. 2015) granting Solazyme's motion for an order confirming the arbitration award rendered by CPR International Institute for Conflict Prevention & Resolution on Feb. 19, 2015, in favor of Solazyme, Inc.

Youzhi Jiagong, (Jun. 8, 2007), "Oil Processing Technology (2nd edition)", Chemical Industry Press, Title page, Publication Page, Table of Contents, pp. 206-213, (in Chinese).

"Linoleic acid and α-linolenic acid are real essential fatty acids", (Mar. 1998), Title page, Publication Page, Table of Contents, Chapter 2: Essential Fatty Acids (pp. 12-13) and Chapter 15: Selection of the most suitable fatty acids (pp. 89-91), with English translation.

Bowman, Barbara A. and Robert M. Russell (eds.), "Present Knowledge in Nutrition" (1st Edition), (Oct. 2004), Title page, Publication Page, Table of Contents, p. 231 (in Chinese).

"Auxenochlorella", article from Wikipedia, Retrieved from the Internet on Mar. 23, 2016, "https://en.wikipedia.org/w/index.php?title=Auxenochlorella&oldid=711518993".

Clore, G.M. and E.M. Chance, A computer analysis of cyanide stimulated oxygen uptake in *Chlorella Protothecoides*. (Jul. 1977) FEBS Lett. 79 (2):353-356.

"Algen—Nudein ais Altmark Spezialitat (Algae noodles: a speciality from Altmark region)" in German language, and other *Chlorella* Food products, (Oct. 9, 2007), 3 pages.

"Aoko's toxin", Aichi Prefectural Institute of Public Health, 6 pages. [Retrieved from the Internet Oct. 13, 2016: <URL: http://www.pref.aichi.jp/eiseiken/5f/bloom_t.html].

Lee, Yuan-Kun, "Commercial Production of microalgae in the Asia-Pacific rim", Journal of Applied Phycology, 9:403-411, (Oct. 29, 1997).

Kay, Robert A., "Microalgae as Food and Supplement", Critical Reviews in Food Science and Nutrition, 30(6):555-573 (Feb. 1991).

Usuki, Riichiro and Luniko Kamata, "Experimental Trials on the Role of Lipids in Good Taste and Good Body of Foods", Research reports of Shokei Gakuin College 53, May 2006, p. 85-90 (in Japanese with English Abstract).

"Chlorella Photosynthesis—Dictionary", last modified Mar. 23, 2015, Retrevied from the Internet: <URL: (http://photosyn.jp/pwiki/index.php?%E3%82%AF%E3%83%AD%E3%83%AC%E3%83%A9) with English Machine Translation.

Hirashima, Ryuta, "Framework of evaluation on inventive step requirement and significance of'technical problem'", Patent 2010, 63(5): 34-49 (in Japanese; no translation).

Ullmann, Jorg, "The Difference between *Chlorella* vulgaris and *Chlorella* pyrenoidosa", (2006) (http://www.algomed.de/index.php?op=algenfarm_geschichte).

"History of the algae farm: Chlorella Algae—Roquette Klötze GmbH", [Retrieved from the Internet Nov. 25, 2016: <URL: (http://www.algomed.de/index.php?op=algenfarm_geschichte)].

Oral Summary, dated Nov. 7, 2016, for Invalidation Hearing for Japanese Patent No. 5731982 (in Japanese).

Oral Summary by the Patentee, dated Nov. 29, 2016, for Invalidation Hearing for Japanese Patent No. 5731982 (in Japanese).

Letter from Ray Matulka to Paulette Gaynor and Sylvester Mosley, dated Apr. 18, 2013, re: Request to Cease Evaluation of GRN 000450, Letter from Ray Matulka to Paulette Gaynor, dated Apr. 18, 2013, re: High Lipid Chlorella protothecoides S106 Flour GRAS Notification and GRAS Exemption Claim (dated Apr. 18, 2013). Solazyme Market and Products, (2005).

Letter from Susan Cho to Susan Carlson, dated Jul. 25, 2011 and "RF1's Chlorella vulgaris GRAS Self affirmation (dated Jul. 16, 2010)."

[Retrieved from the Internet Oct. 13, 2016: <URL: http://hfnet.nih.go.jp/contents/detail105.htm] (in Chinese).

"Roquette Freres, S.A. and Solazyme, Inc. Agree to Dissolve Microalgae Join Venture", (Jun. 24, 2013) Press Release, Lestrem, France.

Standard Tables of Food Composition in Japan 2015 (Seventh Revised Edition), Table of Fatty Acid Composition, Edited by The Council for Science and Technology, the Ministry of Education, Culture, Sports, Science and Technology, (available from http://www.mext.go.jp/a_menu/syokuhinseibun/1365295.htm) [Retrieved from the Internet Oct. 12, 2016: <URL: (http://www.algomed.de/index.php?op=algenfarm_geschichte)] http://www.geocities.jp/jr2bvb/syokuhin/sibousan/oil_s.htm].

"'Taste' of Lipids?" [Retrieved from the Internet Oct. 12, 2016: <URL: (https://sites.google.com/site/coffeetambe/coffeescience/physiology/taste/fat] with English Machine Translation.

*Roquette Freres S.A.* v. *Solazyme Inc.*, Delaware District Court, Case No. 1:14-cv-01442 District Judge Sue L. Robinson, presiding, Solazyme, Inc.'s Answer to Plaintiff Roquette Freres, S.A.'s Complaint, Petition to Confirm Arbitration Award and Counterclaims, filed Feb. 26, 2015, 29 pages.

Joint Venture and Operating agreement of Solazyme Roquette Nutritionals, LLC., copy dated Nov. 7, 2015.

*Solazyme, Inc.* vs. *Roquette Freres, S.A.*, Arbitration Award, dated Feb. 19, 2015.

Request for Invalidation, dated Jan. 7, 2015, for Chinese Patent Application No. 200980149978.1, 21 pages (in Chinese).

Supplemental Statement for Request for Invalidation, dated Dec. 2, 2015, for Chinese Patent Application No. 200980149978.1, 35 pages (in Chinese), including the list of submitted Counter Evidences on p. 1-2.

Notification of Acceptance of Request for Invalidation, dated Jan. 28, 2016, for Chinese Patent Application No. 200980149978,1, 4 pages (in Chinese).

Documents filed by the Petitioner—Part II, dated Apr. 29, 2015, for Chinese Patent Application No. 200980149978.1, 21 pages (in Chinese), including : • Jia, Xuan, et al., "Removal of Total nitrogen form wastewater dischrage from a chemical pertilizer plant by Chlorella protothecoides USTB-01", Chinese Journal of Environmental Engineering, (Apr. 2010), 4(4):737-740 (in Chinese).

Documents filed by the Petitioner—Part III, dated May 5, 2015, for Chinese Patent Application No. 200980149978.1, 21 pages (in Chinese), including : , including : • Singelton Paul and Diana Sainsbury, "Dictionary of Microbiological and Molecular Biology, (3rd Ed. 2006)", p. 155 (and Chinese translation thereof) • Singelton Paul and Diana Sainsbury, "Dictionary of Microbiological and Molecular Biology, (2nd Ed. 1987)", pp. 178-179 (and Chinese translation thereof).

Statement of Grounds & Particulars of Opposition, Grounds for Opposition, In the matter of Australian Patent Application No. 2009303354 in the name of Solazyme, Inc. and Opposition by *Roquette Frères, S.A.* v. *Solazyme, Inc.*, Commonwealth of Australia Mar. 3, 2016, (21 pages).

Declaration of Michael Armin Borowitzka In the matter of Australian Patent Application No. 2009303354 in the name of Solazyme, Inc. and Opposition by *Roquette Frères, S.A.* v. *Solazyme, Inc.*, Commonwealth of Australia Jun. 2, 2016, (32 pages).

• Exhibit MB-1, Federal Court of Australia, Practice Note CM7, Expert Witnesses in Proceedings on the Federal Court of Australia, commenes Jun. 4, 2013 • Exhibit MB-2, Michael Armin Borowitzka Curriculum Vitae • Exhibit MB-3, J. M. Hundley, R. B. Ing and R. W. Krauss, "Algae as Sources of Lysine and Threonine in Supplementing Wheat and Bread Diets", Science, New Series, vol. 124, No. 3221 (Sep. 21, 1956), pp. 536-537. • Exhibit MB-4, Krauss, Robert W., "Mass Culture of Algae for Food and Other Organic Compounds," American Journal of Botany, vol. 49, No. 4 (Apr.

(56) References Cited

OTHER PUBLICATIONS

1962), pp. 425-435. • Exhibit MB-5, Lee, Yuan-Kun, "Commercial Production of microalgae in the Asia-Pacific rim", Journal of Applied Phycology, 9:403-411, (Oct. 29, 1997) • Exhibit MB-6, Soong, Pinnan, "Productions and Development of *Chlorella* and *Spirulina* in Taiwan", Algae Biomass: Production and Use, Gedaliah Shelef and Carl J. Soeder (eds.), North-Holland Biomedical Press, (Dec. 1980), pp. 97-113 and title and copyright page. • Exhibit MB-7, Kawaguchi, Kotaro, "Microalgae Production Systems in Asia", Algae Biomass: Production and Use, Gedaliah Shelef and Carl J. Soeder (eds.), North-Holland Biomedical Press, (Dec. 1980), pp. 25-33 and title and copyright page. • Exhibit MB-8, Kay, Robert A., "Microalgae as Food and Supplement", Critical Reviews in Food Science and Nutrition, 30(6):555-573 (Feb. 1991). • Exhibit MB-9, Raymundo et al., "Fat mimetic capacity of Chlorella vulgaris biomass in oil-in-water food emulsions stabilized by pea protein," Food Research International, 38:961-965, (Feb. 25, 2005). • Exhibit MB-10, Samejima, H. and J Myers, "On the Heterotrophic Growth of Chlorella *pyrenoidosa*", J. Gen Microbiol, (1958), 18:107-117.
• Exhibit MB-11, Aoki, Shigeji and Eiji Hase, "De- and Re-Generation of Chloroplasts in the Cells of Chlorella Protothecoides", Plant & Cell Physiol, (Sep. 5, 1964), vol. 5, pp. 473-484 [Retrieved from the internet on Jun. 7, 2013 from http://pcp.oxfordjournals.org/ by Reprints Desk ]. • Exhibit MB-12, Becker, E.W., "Micro-algae as a source of protein," Biotechnology Advances, 25:207-201, (Mar.-Apr. 2007). • Exhibit MB-13, Iwamoto, Hiroaki, "Industrial Production of Microalgal Cell-mass and Secondary Products— Major Industrial Species Chlorella", Chapter 11, Handbook of Microalgal Culture: Biotechnology and Applied Phycology, Amos Richmond (eds), (Dec. 1, 2003), pp. 255-263. • Exhibit MB-14, Petkov et al., "Which are fatty acids of the green alga Chlorella?," Biochemical Systematics and Ecology, 35:281-285, (2007). • Exhibit MB-15, Gladu, Patricia K., et al. "Sterol, Fatty Acid and Pigment Characteristics of UTEX 2341, a Marine Eustigmatophyte Identified Preivously as Chlorella Minutissuma (Chlorophyceae)" J. Phycol., (Jun. 21, 1995), 31:774-777. • Exhibit MB-16, Xu et al., "High Quality Biodiesel Production From a Microalga Chlorella Protothecoides by Heterotrophic Growth In Fermenters," Journal of Biotechnology, 126(4):499-507, (May 2006). • Exhibit MB-17, Matsuka et al., "Changes in Contents of Carbohydrate and Fatty Acid in the Cells of Chlorella Protothecoidesduring the process of De- and Re-Generation of Chloroplasts," Plant and Cell Physiol., 7:651-662 (Sep. 24, 1966). • Exhibit MB-18, Xuan, J. et al., "Removal of total nitrogen from wastewater discharge from a chemical fertilizer plant by Chlorela protothecoides USTB-01", Chinese Journal of Environmental Engineering, (Apr. 2010), vol. 4, No. 4, pp. 737-740.
• Exhibit MB-19, Australian Application No. 2009303354B2 from International Patent Application No. PCT/US2009/060692, naming Solazyme, Inc., International Patent Publication No. 2010/045368, dated Apr. 22, 2010. • Exhibit MB-20, Pabst, W., "Nutritional evaluation of nonsewage microalgae by the rat balance method," Arch. HyrobioL Beih, (Dec. 1978), pp. 65-70 • Exhibit MB-21, Urano, et al., "Effect of Osmotic Stabilizers on Protoplast Generation on Chlorella ellipsoidea Yellow/White Color Mutants", Journal of Bioscience and Bioengineering, vol. 90, No. 5, 567-569, (2000).
• Exhibit MB-22, Kamiya, "Effects of Blue Light and Ammonia on Nitrogen Metabolism in a Colorless Mutant of Chlorella", Plant Cell Phyiol., 30(4):513-521 (1989) • Exhibit MB-23, Biello et al., "Biofuel of the Future: Oil from Algae," Scientific American, 2 pages, (Jan. 9, 2008).
Evidence in Support, In the matter of Australian Patent Application No. 2009303354 in the name of Solazyme, Inc. and Opposition by *Roquette Frères, S.A.* v. *Solazyme, Inc.*, Commonwealth of Australia, Jun. 3, 2016, (1 page).
Declaration of Young J. Suh In the matter of Australian Patent Application No. 2009303354 in the name of Solazyme, Inc. and Opposition by *Roquette Frères, S.A.* v. *Solazyme, Inc.*, Commonwealth of Australia, Aug. 31, 2016, (94 pages) • Exhibit'YS1, Arbitration Award, *Solazyme Inc.* vs. *Roquette Frères*, Case 1:14-cv-O1442-SLR, Document 153, Filed Dec. 21, 2015 • Exhibit YS2, French Patent Publication No. FR 2 924 126, filed Nov. 28, 2007.
• Exhibit YS3, Memorandum Opinion, Document 153, *Roquette Frères, S.A,* vs. *Solazyme Inc.*, Case 1:14-cv-O1442-SLR, filed Dec. 21, 2015.
Declaration of Craig Patch In the matter of Australian Patent Application No. 2009303354 in the name of Solazyme, Inc. and Opposition by *Roquette Frères, S.A.* v. *Solazyme, Inc.*, Commonwealth of Australia, Sep. 5, 2016, (22 pages) • Exhibit CP-1, Federal Court of Australia, Practice Note CM7, Expert Witnesses in Proceedings on the Federal Court of Australia, commences Jun. 4, 2013. • Exhibit CP-2, Craig Patch Curriculum Vitae.
Declaration of Craig Patch In the matter of Australian Patent Application No. 2009303354 in the name of Solazyme, Inc. and Opposition by *Roquette Frères, S.A.* v. *Solazyme, Inc.*, Commonwealth of Australia, Sep. 28, 2016, (42 pages). • Exhibit CP3, Record of Views Formed in Response to Inquires, updated Mar. 2015 (20 pages) • Exhibit CP4, Huss, V.A.R., et al., "Biochemical Taxonomy and Molecular Phylogeny of the Genus *Chlorella sensu Lato* (Chlorophyta)1", J, Phycol. 35, 587-598 (Jan. 15, 1999).
Evidence in Answer, In the matter of Australian Patent Application No. 2009303354 in the name of Solazyme, Inc. and Opposition by *Roquette Frères, S.A.* v. *Solazyme, Inc.*, Commonwealth of Australia, Sep. 29, 2016, (1 page).
Declaration of Michael Armin Borowitzka In the matter of Australian Patent Application No. 2009303354 in the name of Solazyme, Inc. and Opposition by *Roquette Frères, S.A.* v. *Solazyme, Inc.*, Commonwealth of Australia, Dec. 21, 2016, (14 pages).
Evidence in Reply, In the matter of Australian Patent Application No. 2009303354 in the name of Solazyme, Inc. and Opposition by *Roquette Frères, S.A.* v. *Solazyme, Inc.*, Commonwealth of Australia Dec. 23, 2016, (1 page).
"Roquette's Microalgae High Lipid Algal Flour Wins Most Innovative Food Ingredient at the 2013 Fi Europe Excellence Award," www.PRnewswire.com/news-release/roquettes-migroalgae-high-lipid-algal-flour-wins-most-innovative-food-ingrediant-at-the-2013-fi-europe-excellence-awards, (Nov. 25, 2013), pp. 1-5.
Zhou, Lian-ning et al. "Effects of Environmental Factors on Nitrogen and Phosphorus Removal by *Chlorella vulgaris* in Wastewater", Current Biotechnology, (Jan. 25, 2015), vol. 5, No. 1, Title page, Publication Page, Table of Contents (I Chinese and English), pp. 60-65, with English abstract.
Evidence 1, Explanation paper, filed with IP High Court Case No. H29 (gyo-ke) 10149 on Oct. 6, 2017 in Invalidation Appeal No. 2016-800012 against Japanese Patent No. 5731982, with English translation.
First Statement, Substantive Brief, filed with IP High Court Case No. H29 (gyo-ke) 10149 on Nov. 17, 2017 in Invalidation Appeal No. 2016-800012 against Japanese Patent No. 5731982, with English translation.
Second Statement, Substantive Brief, filed with IP High Court Case No. H29 (gyo-ke) 10149 on Jan. 17, 2018 in Invalidation Appeal No. 2016-800012 against Japanese Patent No. 5731982. With Explanation Paper for the Evidence. Japanese Only.
Opponent's Outline of Submissions, in the Matter of Australian Patent Application No. 2009303354 in the name of Corbion Biotech, Inc., dated Jan. 24, 2018, 48 pages.
Response To Reg 5.23 Request, in the Matter of Australian Patent Application No. 2009303354 in the name of Corbion Biotech, Inc., filed Feb. 5, 2018, 18 pages. • Letter from David Sieveking, dated Jan. 24, 2018 • Statutory Declaration of Dr. Daniel Peter Sieveking, dated Jan. 24, 2018. • Exhibit DS-1, Kyle, David, "Production and Use of Lipids from Microalgae", Microalgal Lipids, Lipid Technology, (May-Jun. 1992), pp. 59-64. • Exhibit DK-2, Chen et al., "High cell density culture of microalgae in heterotrophic growth," Trends In Biotechnology, 14:421-426, (1996).
Consent to Withdraw, dated Feb. 14, 2018, for IP High Court Case No. H29 (gyo-ke) 10149, Invalidation Appeal No. 2016-800012, against Japanese Patent No. 5,731,982, in the names of TerraVia Holdings, Inc. in Japanese Only, [SOLAO043JP-0807X01JP].
Request for Withdrawal of Opposition, by Roquette Freres, to Grant of Australian Patent Application No. 2009303354, in the Name of Corbion Biotech, Inc., dated Mar. 13, 2018.

(56) References Cited

OTHER PUBLICATIONS

Opposition Proceedings, dated Mar. 14, 2018, Acknowledgement of the the Request for Withdrawal of Opposition, by Roquette Freres, to Grant of Australian Patent Application No. 2009303354.
Third Party Observations from Roquette Freres, dated Aug. 31, 2017, for Chinese patent for invention No. 200980149978.1 (in Japanese with English Translation).
Third Party Observations from Roquette Freres, dated Aug. 31, 2017, for Chinese patent for invention No. 201080026237.7 (in Japanese with English Translation).
Chacón-Lee et al., "Microalgae for "Healthy" Foods—Possibilities and Challenges," *Comp. Rev. Food Sci. and Safety*, 9: 655-675 (2010).
"Enter the World of Microalgae," Roquette (Jun. 2014).
International Bureau, International Preliminary Report on Patentability in International Application No. PCT/EP2014/056125, dated Sep. 29, 2015.
International Bureau, International Search Report in International Application No. PCT/EP2014/056125, dated Sep. 20, 2014.
U.S. Appl. No. 14/779,365, filed Sep. 23, 2015.
"Full Report (All Nutrients) 01001, Butter, salted," *USDA National Nutrient Database for Standard Reference*, Release 28, Jan. 25, 2016 (5 pgs).
Kirk, J. et al., "Mastitis Control Program for Prototheca Mastitis in Dairy Cows," (2001).

\* cited by examiner

MICROALGAL BIOMASS PROTEIN ENRICHMENT METHOD

CROSS-REFERENCE TO RELATED APPLICATIONS

This application in a continuation of U.S. patent application Ser. No. 14/779,365, filed Sep. 23, 2015, entitled "MICROALGAL BIOMASS PROTEIN ENRICHMENT METHOD", which is the U.S. National State Application of International Patent Application No. PCT/EP2014/056125, filed Mar. 27, 2014.

The present invention relates to a method of protein enrichment of microalgal biomass, said microalga being more particularly of the genus *Chlorella*, even more particularly of the species *Chlorella sorokiniana* or *Chlorella protothecoides*.

Algae—macroalgae and microalgae—have a specific but largely unexplored richness. Their use in the production of food, chemicals and bioenergy remains very rare. They conceal, however, components of great value, whose richness and abundance can be truly appreciated only by the marine animals that feed on them.

Microalgae are in fact sources of vitamins, lipids, proteins, sugars, pigments and antioxidants.

Algae and microalgae are thus of interest to the industries that use them to produce dietary supplements, functional foods, cosmetics or medicines, or for aquaculture.

Microalgae are above all photosynthetic microorganisms which colonize all biotopes exposed to light.

On an industrial scale, their monoclonal culturing is carried out in photobioreactors (autotrophic conditions: with light and $CO_2$) or, for some, also in fermentors (heterotrophic conditions: in darkness in the presence of a carbon source).

A few microalgae species are in fact able to grow in the absence of light: *Chlorella, Nitzschia, Cyclotella, Tetraselmis, Crypthecodinium, Schizochytrium*.

Furthermore, it is estimated that culturing under heterotrophic conditions costs ⅒ that of culturing under phototrophic conditions because, for the skilled person, heterotrophic conditions make it possible to:
- use fermentors that are identical to those used for bacteria and yeasts and that allow all of the culture parameters to be controlled.
- produce biomasses in much greater amounts than those obtained by light-based culturing.

The profitable use of microalgae generally requires control of the fermentation conditions so as to accumulate the components of interest, such as:
- pigments (chlorophyll a, b and c, β-carotene, astaxanthin, lutein, phycocyanin, xanthophylls, phycoerythrin, etc.) increasingly in demand for their remarkable antioxidant properties and for providing natural colors in foods,
- proteins, in order to optimize their nutritive qualities; or
- lipids, in order to optimize their fatty acid content (up to 60%, even 80% by weight of their dry matter), in particular for:
  - biofuel applications, but also
  - human or animal food applications, when the selected microalgae produce so-called "essential" (i.e., provided in the diet because they are not naturally produced by humans or animals) polyunsaturated fatty acids, or PUFAs.

To arrive at this result, first high cell density (HCD) fermentation methods were thus thoroughly investigated, so as to obtain maximum yields and productions of proteins or lipids.

The objective of these HCD cultures was to obtain the desired product in the highest possible concentration in the shortest amount of time.

This precept is verified, for example, for the biosynthesis of astaxanthin by *Chlorella zofingiensis*, where the growth of the microalga proved to be directly correlated with the production of this compound (Wang and Peng, 2008, *World J Microbiol. Biotechnol.*, 24(9), 1915-1922).

However, the fact of maintaining growth at its maximum rate ($\mu$, in $h^{-1}$) is not always correlated with high production of the desired product.

In fact, it quickly became apparent to the specialists in the field that, in order for microalgae to produce large lipid reserves, it is necessary, for example, to subject the microalgae to a nutritional stress that limits their growth.

Now, growth and production are decoupled in fermentation methods.

For example, to promote the accumulation of polyunsaturated fatty acids (here docosahexaenoic acid, or DHEA), patent application WO 01/54510 advises to dissociate cell growth and polyunsaturated fatty acid production.

In the microalga *Schizochytrium* sp. strain ATCC 20888, a first growth phase without oxygen limiting is thus carried out so as to promote the production of a high cell density (greater than 100 g/l); then, in a second step, the oxygen supply is gradually reduced so as to stress the microalga, to slow its growth and to initiate the production of the fatty acids of interest.

In the microalga *Crypthecodinium cohnii*, the highest docosahexaenoic acid (DHEA, polyunsaturated fatty acid) content is obtained with a low glucose concentration (about 5 g/l), and thus with low a growth rate (Jiang and Chen, 2000, *Process Biochem.*, 35(10), 1205-1209).

These results illustrate clearly that the kinetics of product formation can be positively or negatively associated with microalgae growth, and even a combination of the two.

Consequently, in the case where product formation is not correlated with high cell growth, it is wise to control the cell growth rate.

In general, the skilled person chooses to control microalgae growth by controlling the fermentation conditions (Tp, pH, etc.) or by controlling the supply of nutritional components to the fermentation medium (semi-continuous so-called "fed-batch" conditions).

If the skilled person chooses to control microalgae growth under heterotrophic conditions by means of the supply of carbon sources, he or she generally chooses to adapt the carbon source (pure glucose, acetate, ethanol, etc.) to the microalga (*C. cohnii, Euglena gracilis*, etc.) according to the metabolite produced (a DHEA-type polyunsaturated fatty acid, for example).

The temperature may be a key parameter as well:
  it has been reported, for example, that the synthesis of polyunsaturated fatty acids by certain microalgae species, such as EPA by *Chlorella minutissima*, is promoted at a temperature lower than that required for the optimal growth of said microalga;
  conversely, the yield of lutein by *Chlorella protothecoides* grown heterotrophically is higher when the production temperature is increased from 24° C. to 35° C.

*Chlorella protothecoides* is justifiably recognized as one of the best oil-producing microalgae.

Under heterotrophic conditions, it quickly transforms carbohydrates into triglycerides (greater than 50% of its dry matter).

To optimize this triglyceride production, the skilled person is led to optimize the carbon flux toward the production of oil by acting on the nutritional environment of the fermentation medium.

It is thus known that oil accumulates when a sufficient amount of carbon is supplied, but under nitrogen-deficient conditions.

The C/N ratio is thus decisive here, and it is acknowledged that the best results are obtained by acting directly on the nitrogen content, as the glucose content is not limiting.

Not surprisingly, this nitrogen deficiency affects cell growth, resulting in a growth rate that is 30% lower than the normal microalgal growth rate (Xiong et al., *Plant Physiology*, 2010, 154, pp. 1001-1011).

To explain this result, Xiong et al., in the above-mentioned article, show that, in fact, if the *Chlorella* biomass is divided into its five principal components, i.e., carbohydrates, lipids, proteins, DNA and RNA (representing 85% of its dry matter), if the C/N ratio has no impact on the DNA, RNA and carbohydrate content, it becomes preeminent for the protein and lipid content.

Thus it is that *Chlorella* cells grown with a low C/N ratio contain 25.8% proteins and 25.23% lipids, while a high C/N ratio enables the synthesis of 53.8% lipids and 10.5% proteins.

To optimize oil production, it is thus essential for the skilled person to control the carbon flux by diverting it toward oil production, to the detriment of protein production; the carbon flux is redistributed and accumulates in lipid storage substances when the microalgae are placed in nitrogen-deficient medium.

Armed with this teaching, to produce protein-rich biomasses the skilled person is thus led to carry out the opposite of this metabolic control, i.e., to apply fermentation conditions that promote a low C/N ratio instead, and thus:
  to supply to the fermentation medium a large amount of the nitrogen source, while maintaining constant the load of the carbon source that will be converted into proteins; and
  to stimulate the growth of the microalga.

It is a matter of modifying the carbon flux toward the production of proteins (and thus of biomasses), to the detriment of the production of storage lipids.

In the context of the invention, the Applicant company chose to explore a novel pathway by disclosing an alternative solution to that traditionally envisaged by the skilled person.

Thus, the invention relates to a method of protein enrichment of a microalga grown heterotrophically, said microalga being of the genus *Chlorella*, more particularly *Chlorella sorokiniana* or *Chlorella protothecoides*, said heterotrophic culturing method comprising a step aiming at limiting the growth of said microalga by means of a deficiency in the fermentation medium of a non-nitrogenous nutritional source.

This step is a heterotrophic culturing step where a non-nitrogenous nutritive factor is supplied in the medium in an amount that is insufficient to allow the microalga to grow. It should be noted that "amount that is insufficient" does not mean that this nutritive factor is not supplied. The result of this nutrient-deficient phase is to slow (to limit) cell metabolism, without inhibiting it completely.

In the meaning of the invention, "enrichment" refers to an increase in the protein content of the biomass of at least 15%, preferably at least 20% by weight, so that the protein content of the biomass reaches more than 50% by weight.

The invention covers more specifically a method of heterotrophic culturing of said microalgae comprising a step aiming at limiting the growth of said microalga by means of a deficiency in the fermentation medium of a non-nitrogenous nutritional source.

The present invention thus relates to a method of protein enrichment of a microalga grown heterotrophically, said microalga being of the genus *Chlorella*, more particularly *Chlorella sorokiniana* or *Chlorella protothecoides*, the method comprising heterotrophic culturing that includes a step aiming at limiting the growth of said microalga by means of a deficiency in the fermentation medium of a non-nitrogenous nutritional source, thus enabling the biomass protein content to reach more than 50% by weight.

By "deficiency in the fermentation medium of a non-nitrogenous nutritional source" is meant a culture wherein at least one of the non-nitrogenous nutritive factors is supplied to the microalga in an amount that is insufficient for it to grow.

In particular, the nutritional source is deficient so as to obtain a growth rate that is 10% to 60% lower than the growth rate with no limiting of said nutritional source. In particular, it is disclosed to decrease the growth rate by 10% to 60% compared with the growth rate with no limiting of glucose, in particular by 10%, 15%, 20%, 25%, 30%, 35%, 40%, 45%, 50% or 55% compared with the growth rate with no limiting of glucose. Preferably, the growth rate is decreased by 15% to 55%.

The duration of the culturing phase comprising a deficiency of a nutritive factor, in particular of glucose, is at least 1 h, preferably at least 10 h, more preferably at least 20 h, in particular between 30 h and 60 h.

The result is an absence of residual non-nitrogenous nutritive factor in the culture medium, the microalga consuming this nutritive factor as fast as it is supplied. However, the absence of residual non-nitrogenous nutritive factor in the culture medium is distinguished from a situation in which the microalga is completely deprived of the nutritive factor.

In the context of the invention, the essential criterion is thus the limiting of cell growth induced by stress, namely cellular stress caused by the deficiency in the fermentation medium of a non-nitrogenous nutritive substance.

This strategy is thus quite counter to the technical prejudice according to which, in order to increase the protein content of the biomass, it is inevitably necessary to increase the biomass and thus increase cell growth.

By "a non-nitrogenous nutritional source" is meant a nutritive substance selected, for example, from the group consisting of glucose and phosphates.

As will be exemplified below, it may be advantageously chosen to limit the growth of:
  *Chlorella sorokiniana* by means of a glucose deficiency in the fermentation medium,
  *Chlorella protothecoides* by means of a phosphate deficiency in the fermentation medium.

In particular, for these strains, the nutritive substance is supplied so as to obtain a growth rate of between $0.06\ h^{-1}$ and $0.09\ h^{-1}$.

In a very specific embodiment, the *Chlorella sorokiniana* strain is the strain UTEX 1663 (The Culture Collection of Algae at the University of Texas at Austin, USA). In a very specific embodiment, the *Chlorella protothecoides* strain is the strain CCAP211/8D (The Culture Collection of Algae and Protozoa, Scotland, UK).

Optionally, the growth of said microalga can be limited by adding in the culture medium substances that inhibit cell growth, such as sulfates.

Furthermore, without being bound to any one theory, the Applicant company has found that the glucose flux in microalgae of the genus *Chlorella sorokiniana* is normally used according to a quite precise prioritization:
1. basal metabolism,
2. growth, i.e., formation of a protein-rich biomass,
3. storage substances (lipids and carbohydrates such as starch).

This principle explains the natural variations in protein content as the microalga grows, despite the constant supply of nitrogen.

The Applicant company has thus found that in order to enrich the microalgal biomass in proteins it is necessary to limit the growth of the microalga and to control its consumption of nutritive sources other than nitrogen, for example glucose, so as to:
dedicate the entire consumption of glucose to protein production pathways,
avoid the accumulation of storage substances such as lipids.

Indeed, avoiding a nitrogen deficiency makes it possible to prevent the diversion of metabolic fluxes toward the production of lipids.

Optionally, it may be advantageous to go so far as to completely block any synthesis of storage material, by the use of specific inhibitors.

Indeed, a certain number of inhibitors of the synthesis pathway for lipids, and even for starch (the storage carbohydrate par excellence of green microalgae), are known:
for lipids, cerulenin is described as an inhibitor of fatty acid synthesis, and lipstatin, a natural substance produced by *Streptomyces toxytricini*, as an inhibitor of lipases, etc.;
for starch, iminosugars (obtained by simple substitution of the endocyclic oxygen atom of sugars with a nitrogen atom) are historically known as powerful inhibitors of glycosidases, glycosyltransferases, glycogen phosphorylases and UDP-Galp mutase.

Thus, the method comprises the fermentation of a microalgal biomass under heterotrophic conditions with a first step of growing the biomass and a second step of depriving the fermentation medium of a non-nitrogenous nutritional source.

This second step makes it possible to enrich the biomass in protein. In particular, it makes it possible for the protein content of the biomass to reach more than 50% by weight (by weight of dry matter).

In a first preferred embodiment in accordance with the invention, the method for heterotrophically culturing said microalgae, in particular *Chlorella sorokiniana*, comprises:
a first step in which the microalgae are grown, where the glucose supply rate is adjusted to the consumption capacity of said microalgae so as to obtain a large biomass quickly,
a second step in which the microalgae produce proteins, where the glucose supply rate is set to a value distinctly below the glucose consumption capacity of said microalgae so as to prevent the additional accumulation of storage substances or to promote their consumption.

As will be exemplified below, the first step in which the microalgae are grown is carried out in a discontinuous or "batch" mode in which the entirety of the initial glucose supply is consumed by the microalga, resulting in the production of a base biomass.

The second step in which proteins are produced is carried out under conditions in which:
either: complete medium is supplied semi-continuously, using a so-called "fed-batch" system, after the initial glucose supply is consumed; the other operational parameters of the fermentation remain unchanged.

Glucose is supplied continuously and the supply rate is then lower than the strain's maximum rate of consumption so that the residual glucose content in the medium is kept at zero.

The strain's growth is thus limited by the availability of glucose (glucose-limiting condition).
or: a continuous chemostat operation is used, in which the strain's growth rate ($\mu$) is kept at its minimum value, the strain's growth being limited by the glucose supply.

This method of operation makes it possible to obtain a biomass with a high protein content thanks to the limiting of glucose and to the low growth rate imposed, all while ensuring very good productivity.

In a second preferred embodiment in accordance with the invention, the method for heterotrophically culturing said microalgae, in particular *Chlorella protothecoides*, comprises a step in which the microalgae are grown, where a limiting of the phosphate supply limits the growth rate and results in an increase in the protein content. Thus, the heterotrophic culturing of microalgae of the species *Chlorella protothecoides* comprises a step of heterotrophic culturing with a deficiency of phosphates, the growth rate thus being reduced and resulting in an increase in the protein content.

The invention will be better understood with the aid of the following examples, which are meant to be illustrative and non-limiting.

EXAMPLES

Example 1: Production of *Chlorella sorokiniana* Using Sequential-Batch Fermentation without Limiting the Supply of Nutritive Medium The strain used is a *Chlorella sorokiniana* (strain UTEX 1663—The Culture Collection of Algae at the University of Texas at Austin, USA).

Preculture 600 ml of medium in a 2 l Erlenmeyer flask;
Composition of the medium (Table 1 below)

TABLE 1

| Macroelements (g/l) | Glucose | 20 |
|---|---|---|
| | $K_2HPO_4 \cdot 3H_2O$ | 0.7 |
| | $MgSO_4 \cdot 7H_2O$ | 0.34 |
| | Citric acid | 1.0 |
| | Urea | 1.08 |
| | $Na_2SO_4$ | 0.2 |
| | $Na_2CO_3$ | 0.1 |
| | Clerol FBA 3107 (defoamer) | 0.5 |
| Microelements (mg/l) | $Na_2EDTA$ | 10 |
| | $CaCl_2 \cdot 2H_2O$ | 80 |
| | $FeSO_4 \cdot 7H_2O$ | 40 |
| | $MnSO_4 \cdot 4H_2O$ | 0.41 |
| | $CoSO_4 \cdot 7H_2O$ | 0.24 |
| | $CuSO_4 \cdot 5H_2O$ | 0.24 |
| | $ZnSO_4 \cdot 7H_2O$ | 0.5 |
| | $H_3BO_3$ | 0.11 |
| | $(NH_4)_6Mo_7O_{27} \cdot 4H_2O$ | 0.04 |

The pH is adjusted to 7 before sterilization by adding 8 N NaOH.

Incubation proceeds under the following conditions:
duration: 72 h;
temperature: 28° C.;
shaking speed: 110 rpm (Infors Multitron incubator).

The preculture is then transferred to a 30 l Sartorius fermentor.

Biomass Production Culture

The medium is identical to that of the preculture, but the urea is replaced with NH$_4$Cl.

TABLE 2

| Macroelements (g/l) | Glucose | 20 |
|---|---|---|
| | K$_2$HPO$_4$•3H$_2$O | 0.7 |
| | MgSO$_4$•7H$_2$O | 0.34 |
| | Citric acid | 1.0 |
| | NH$_4$Cl | 1.88 |
| | Na$_2$SO$_4$ | 0.2 |
| | Clerol FBA 3107 (defoamer) | 0.5 |
| Microelements (mg/l) | Na$_2$EDTA | 10 |
| | CaCl$_2$ | 80 |
| | FeSO$_4$•7H$_2$O | 40 |
| | MnSO$_4$•4H$_2$O | 0.41 |
| | CoSO$_4$•7H$_2$O | 0.24 |
| | CuSO$_4$•5H$_2$O | 0.24 |
| | ZnSO$_4$•7H$_2$O | 0.5 |
| | H$_3$BO$_3$ | 0.11 |
| | (NH$_4$)$_6$Mo$_7$O$_{27}$•4H$_2$O | 0.04 |

The initial volume ($V_i$) of the fermentor is adjusted to 13.5 l after inoculation.

It is increased to a final volume of 16-20 l.

The operational parameters of the fermentation are as follows:

TABLE 3

| Temperature | 28° C. |
|---|---|
| pH | 5.0-5.2 using 28% NH$_3$ (w/w) |
| pO$_2$ | >20% (maintained by shaking) |
| Shaking speed | Minimum 300 rpm |
| Air flow rate | 15 l/min |

When the initially supplied glucose is consumed, a medium identical to the initial medium, without the defoamer, is supplied in the form of a concentrated solution containing 500 g/l of glucose and—in the same proportions relative to glucose as in the initial medium—the other elements, so as to obtain in the fermentor a glucose content of 20 g/l.

Two other identical additions are supplied in the same manner each time the residual glucose concentration becomes zero.

Clerol FBA 3107 defoamer is added as needed to avoid excessive foaming.

Results

After 46 h of culturing, 38 g/l of biomass is obtained with a protein content (evaluated by N 6.25) of 36.2%.

Example 2: Production of *C. sorokiniana* Using Fed-Batch Fermentation with a Limiting Supply of Glucose In this example, a supply of complete medium (fed-batch mode) is started after the initially supplied glucose is consumed. The other operational parameters of the fermentation remain unchanged.

Glucose is supplied continuously using a 500 g/l concentrated solution. The supply rate is lower than the strain's maximum consumption rate so that the residual glucose content in the medium is kept at zero, i.e., the strain's growth is limited by the availability of glucose (glucose-limiting condition).

This rate increases exponentially over time. The formula used to calculate the addition flow rate is characterized by a factor µ corresponding to the growth rate that the strain can adopt if it consumes all the glucose supplied:

$$S = So \times \exp(\mu \cdot t)$$

S=glucose supply flow rate (in g/h).

So=initial glucose supply flow rate, determined according to the biomass present at the end of the batch. It is 12 g/h under our conditions.

µ=flow rate acceleration factor. It should be below 0.11 h$^{-1}$, which is the strain's growth rate in the absence of nutritional limiting.

t=duration of the fed-batch operation (in h).

The salts are supplied continuously, if possible, separately or mixed with glucose. But they may also be supplied sequentially in several portions.

Table 4 below gives the salt requirements for 100 g of glucose.

TABLE 4

| Macroelements (g) | Glucose | 100 |
|---|---|---|
| | K$_2$HPO$_4$•3H$_2$O | 6.75 |
| | MgSO$_4$•7H$_2$O | 1.7 |
| | Citric acid | 5.0 |
| | Na2SO4 | 1.0 |
| Microelements (mg) | Na$_2$EDTA | 50 |
| | CaCl$_2$•2H$_2$O | 400 |
| | FeSO$_4$•7H$_2$O | 200 |
| | MnSO$_4$•4H$_2$O | 2.1 |
| | CoSO$_4$•7H$_2$O | 1.2 |
| | CuSO$_4$•5H$_2$O | 1.2 |
| | ZnSO$_4$•7H$_2$O | 2.5 |
| | H$_3$BO$_3$ | 0.6 |
| | (NH$_4$)$_6$Mo$_7$O$_{27}$•4H$_2$O | 0.2 |

The concentrations of the elements other than glucose were determined so as to be in excess relative to the strain's nutritional requirements.

Clerol FBA 3107 defoamer is added as needed to avoid excessive foaming.

Results: Effect of the Glucose Supply Rate During the Fed-Batch Operation

Tests were carried out at various glucose supply rates in fed-batch mode. They are characterized by the µ applied. The biomass protein content obtained is evaluated by measuring the total nitrogen expressed in N 6.25.

TABLE 5

| Test | µ fed (h$^{-1}$) | Duration (h) | Biomass (g/l) | Productivity (g/l/h) | % N 6.25 |
|---|---|---|---|---|---|
| 1 | 0.06 | 78 | 43.6 | 0.56 | 49.2 |
| 2 | 0.07 | 54 | 35.1 | 0.65 | 43.1 |
| 3 | 0.09 | 48 | 64.9 | 1.35 | 39.3 |

These results show that glucose-limiting makes it possible to increase the protein content.

Indeed, it is observed that, even with a high µ of 0.09, the protein content obtained is higher than that obtained without limiting, as in Example 1 (39.3% versus 36.2%).

Tighter limiting of the metabolism by means of glucose results in an additional increase in protein content.

Under these test conditions, it is necessary to impose on the strain a p below 0.06 h$^{-1}$ in order to obtain a protein content above 50%.

It should be noted that this condition goes hand in hand with a decrease in productivity: 0.56 g/l/h versus 1.35 g/l/h in test 3.

Example 3: Production of *C. sorokiniana* Using Continuous Chemostat Fermentation with a Limiting Supply of Glucose In this example, a 2 l Sartorius Biostat B fermentor is used.

Fermentation is carried out as in Example 2, but with volumes ⅟₁₀ the size: the volume of inoculum is 60 ml and the initial volume is 1.35 l.

The continuous supply of medium is started according to the same principle as in Example 2, the salts being in this case mixed with glucose in the feed tank. The supply rate is accelerated according to the same exponential formula as in Example 2 by applying a μ of 0.06 h$^{-1}$.

Chemostat

When a volume of 1.6 l is reached (a biomass concentration of about 50 g/l), the continuous chemostat-type operation begins:

1. The fermentor is fed continuously at a flow rate of 96 ml/h with a nutritive medium solution, containing 100 g/l of glucose, of the following composition:

TABLE 6

| Macroelements (g/l) | Glucose | 100 |
|---|---|---|
| | K$_2$HPO$_4$·3H$_2$O | 6.75 |
| | MgSO$_4$·7H$_2$O | 1.7 |
| | Citric acid | 5.0 |
| | Na$_2$SO4 | 1.0 |
| Microelements (mg/l) | Na$_2$EDTA | 50 |
| | CaCl$_2$·2H$_2$O | 400 |
| | FeSO$_4$·7H$_2$O | 200 |
| | MnSO$_4$·4H$_2$O | 2.1 |
| | CoSO$_4$·7H$_2$O | 1.2 |
| | CuSO$_4$·5H$_2$O | 1.2 |
| | ZnSO$_4$·7H$_2$O | 2.5 |
| | H$_3$BO$_3$ | 0.6 |
| | (NH$_4$)$_6$Mo$_7$O$_{27}$·4H$_2$O | 0.2 |

The concentrations of the elements other than glucose were determined so as to be in excess relative to the strain's nutritional requirements.

2. Medium is removed continuously from the fermentor by means of a siphon tube connected to a pump, so as to keep the culture volume at 1.6 l.

Thus, a 0.06/l fraction (6%) of the medium is replaced per hour. This replacement rate is called the dilution rate (D).

In accordance with the principle of the chemostat culturing method, the strain's growth rate (μ) is established at the same value because the strain's growth is limited by the glucose supply:

$$D = \mu = 0.06 \ h^{-1}$$

Results

After 97 h of operation in chemostat mode, the biomass concentration stabilizes at 48 g/l±2 g/l and the protein content at 53±2%.

This mode of operation makes it possible to obtain a biomass with a high protein content thanks to the limiting of glucose and to the low growth rate imposed, all while ensuring very good productivity, of about 2.9 g/l/h, thanks to the high concentration of biomass.

Example 4: Production of *Chlorella protothecoides* Using Batch Fermentation with or without Limiting of the Phosphate Supply The strain used is *Chlorella protothecoides* (strain CCAP21 1/8D—The Culture Collection of Algae and Protozoa, Scotland, UK).

Preculture 150 ml of medium in a 500 ml Erlenmeyer flask;

Composition of the medium: 40 g/l of glucose+10 g/l of yeast extract.

Incubation proceeds under the following conditions: duration: 72 h; temperature: 28° C.; shaking speed: 110 rpm (Infors Multitron incubator).

The preculture is then transferred to a 2 l Sartorius Biostat B fermentor.

Biomass Production Culture

The composition of the culture medium is as follows (in g/l):

TABLE 7

| Glucose | 80 |
|---|---|
| Citric acid | 4 |
| NH$_4$CL | 2 |
| KH$_2$PO$_4$ | 2 (test 1) |
| | or 3 (test 2) |
| Na$_2$HPO$_4$ | 2 (test 1) |
| | or 3 (test 2) |
| MgSO$_4$, 7H$_2$O | 1.5 |
| NaCl | 0.5 |
| Yeast extract | 5 |

The phosphate supply is calculated so as to be limiting in test 1 and in excess in test 2. Clerol FBA 3107 defoamer is added as needed to avoid excessive foaming. The initial volume (V$_i$) of the fermentor is adjusted to 1 l after inoculation.

The operational parameters of the fermentation are as follows:

TABLE 8

| Temperature | 28° C. |
|---|---|
| pH | 6.5 using 28% NH$_3$ (w/w) |
| pO$_2$ | >20% (maintained by shaking) |
| Shaking speed | Minimum 200 rpm |
| Air flow rate | 1 l/min |

Results

TABLE 9

| Test | Duration (h) | Biomass (g/l) | Cumulative $\mu$ (h$^{-1}$) | Residual PO$_4$ (mg/l) | % N 6.25 |
|---|---|---|---|---|---|
| 1 | 45 | 36.5 | 0.07 | 0 | 56.1 |
| 2 | 36 | 38.1 | 0.09 | 800 | 48.1 |

These results show that a limiting of the phosphate supply, confirmed by the absence of residual phosphate at the conclusion of the fermentation, limits the growth rate (measured by the cumulative $\mu$) and, like the limiting of glucose in the preceding examples, results in an increase in the protein content reaching values distinctly greater than 50%.

The invention claimed is:

1. A method of increasing protein content of microalgae grown heterotrophically, the method comprising heterotrophically culturing microalgae of the genus *Chlorella* in a fermentation medium comprising a limiting concentration of phosphate to control a growth rate that is 10% to 60% lower than the growth rate without limiting said phosphate, wherein residual phosphate in the fermentation medium is zero at the end of a fermentation run, and producing a biomass protein content of greater than 50% by weight, wherein the method increases the biomass protein content by weight.

2. The method of claim 1, wherein the microalgae is cultured to obtain the growth rate of between 0.06 h$^{-1}$ and 0.09 h$^{-1}$.

3. The method of claim 1, wherein the microalgae of the genus *Chlorella* is selected from the group consisting of *Chlorella sorokiniana* and *Chlorella protothecoides*.

4. The method of claim 1, wherein the microalgae is cultured for a period of about 30-60 hours.

5. The method of claim 1, wherein the microalgae is *Chlorella protothecoides*.

6. The method of claim 1, comprising culturing microalgae of the genus *Chlorella* in a fermentation medium comprising a limiting concentration of phosphate to control the growth rate that is 15% to 55% lower than the growth rate without limiting said phosphate.

7. The method of claim 1, wherein the microalgae is cultured for a period of at least 1 h.

8. The method of claim 1, wherein the microalgae is cultured for a period of at least 10 h.

9. The method of claim 1, wherein the microalgae is cultured for a period of at least 20 h.

* * * * *